United States Patent [19]
Mills et al.

[11] Patent Number: 5,653,687
[45] Date of Patent: Aug. 5, 1997

[54] METHOD AND APPARATUS FOR SEALING IMPLANTABLE, MEMBRANE ENCAPSULATION

[75] Inventors: John F. Mills, Wakefield, R.I.; Edward J. Doherty, Mansfield, Mass.; Tyrone F. Hazlett, Coventry, R.I.; Keith E. Dionne, Menlo Park, Calif.; Nicholas F. Warner, Belmont; Brian M. Cain, Everett, both of Mass.; David H. Rein, Providence, R.I.

[73] Assignee: Brown University Research Foundation, Providence, R.I.

[21] Appl. No.: 490,112

[22] Filed: Jun. 6, 1995

Related U.S. Application Data

[63] Continuation-in-part of Ser. No. 082,407, Jun. 23, 1993, abandoned.

[51] Int. Cl.⁶ .................................................. A61M 31/00
[52] U.S. Cl. ......................... 604/57; 604/891.1; 424/424; 128/898
[58] Field of Search ........................ 604/93, 8–10, 604/175, 185, 890.1, 132, 57, 891.1; 128/749–755, 762, 898; 435/179, 180, 182, 288, 240.22; 264/4; 425/382.2; 424/424

[56] References Cited

U.S. PATENT DOCUMENTS

| 3,615,024 | 10/1971 | Michaels . | |
|---|---|---|---|
| 3,987,790 | 10/1976 | Eckenhoff et al. | 604/892.1 |
| 4,352,883 | 10/1982 | Lim . | |
| 4,353,888 | 10/1982 | Sefton . | |
| 4,378,016 | 3/1983 | Loeb | 424/424 |
| 4,402,694 | 9/1983 | Ash et al. | 604/891.1 |
| 4,976,966 | 12/1990 | Theeuwes et al. | 424/473 |
| 5,158,881 | 10/1992 | Aebischer et al. | 435/182 |
| 5,182,111 | 1/1993 | Aebischer et al. | 424/424 |

FOREIGN PATENT DOCUMENTS

| 188309 | 1/1986 | European Pat. Off. . |
|---|---|---|
| WO93/00063 | 1/1993 | WIPO . |

OTHER PUBLICATIONS

J. Altman et al. Sucessful Pancreatic Xenografts Using Semipermeable Membrane, 5 Artificial Organs (Suppl.) 776 (1981).

J. Altman, Long–Term Plasma Glucose Normalization in Experimental Diabetic Rats with Macroencapsulated Implants of Benign Human Insulinomas, 35 Diabetes 625(1986).

B. Dupuy, et al. In situ Polymerization of a Microencapsulating Medium Round Living Cells, 22 J. Biomed. Materials Res. 1061 (1988).

W. Hymer et al. Pituitary Hollow Fiber Units In Vivo and In Vitro, 32 Neuroendocrinology 33 9 (1981).

(List continued on next page.)

*Primary Examiner*—Vanitha M. Alexander
*Attorney, Agent, or Firm*—Ivor R. Elrifi; Leon R. Yankwich; Gregory J. Cohan

[57] ABSTRACT

A sealed, implantable, encapsulation device (20) for diffusing a biologically active product or function to an individual which includes a substantially non-porous fitting (32) including an inner surface (33) defining an access port (34). A permselective, porous, membrane (21), having an interior surface (22), cooperates with the fitting inner surface (33) to form a storage cavity (23) therebetween. The membrane interior surface (22) is in substantially cell-tight dry sealing engagement with fitting (32) to seal cavity (23). Living cells (24) are disposed in the cavity (23) which are capable of secreting the biologically active product to an individual. The membrane (21) is of a material capable of permitting the passage of substances between the individual and cells required to provide the biological product or function. A plug member (35) is positioned in the access port (34) and seated in cell-tight sealing engagement with the fitting inner surface (33). A method for sealing the implantable encapsulation device (20) is also provided.

17 Claims, 7 Drawing Sheets

OTHER PUBLICATIONS

H. Iwata et al. The Use of Photocrosslinkable Polyvinyl Alcohol in the Immunoisolation of Pancreatic Islets, 22 Transplant Proceedings 797 (Apr. 1990).

Y. Kojima et al. Xenogeneic Pancreatic Islet Transplantation Using a Millipore Diffusion Chamber, 19 Transplant Proceedings 981 (Feb. 1987).

P. Lamberton et al. Use of Semiipermeable Polyurethane Hollow Fibers for Pituitary Organ Culture, 24 In vitro Cellular & Developmental Biology 500 (Jun. 1988).

Lum et al. Intraperitoneal Nucleopore Chambers: a Murine Model for Allograft Rejection, 20 Transplant Proceedings 173 (Apr. 1988).

S. Ronel et al. Macroporous Hydrogel Membranes for a Hybrid Artificial Pancreas, 17 J. Boimed. Materials Res. 855 (1983).

N. Theodorou et al. Problems in teh Use of Polycarbonate Diffusion Chambers for Syngeneic Pancreatic Islet Transplantation in Rats, 18 Diabetologia 313 (1980).

F. Wong et al. Effects of Thymus Enclosed in Millipore Diffusion Envelopes on Thymectomized Hamsters, 28 Blood 40 (1966).

G. Zondervan et al. Design of a Polyurethane Membrane for the Encapsulation of Islets of Langerhans, 13 Biomaterials 136 (1992).

Y. Shirai et al. Development of Polymeric Shape Memory Material, Mitsubishi Technical Bulletin n. 184 (Dec. 1988).

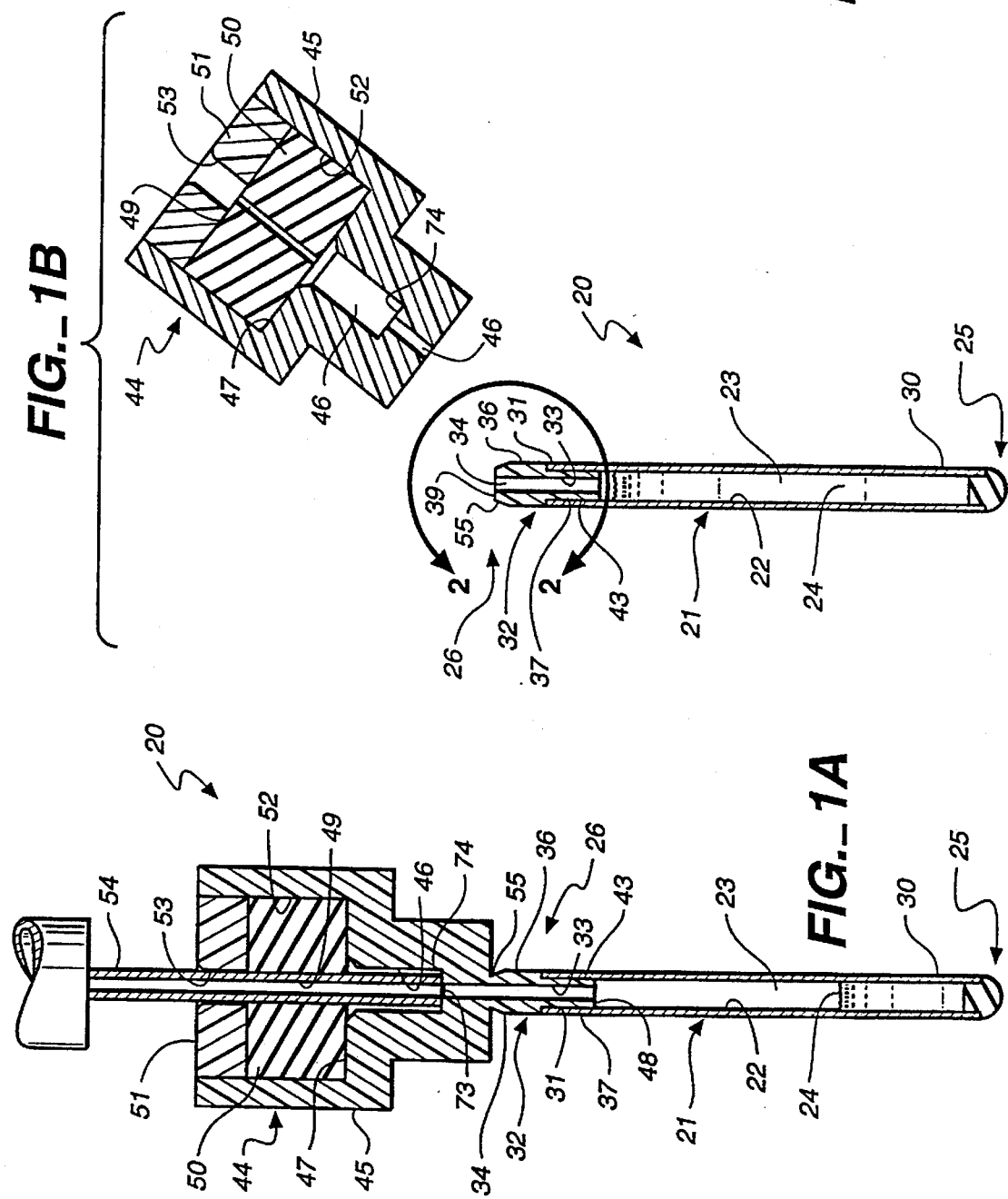

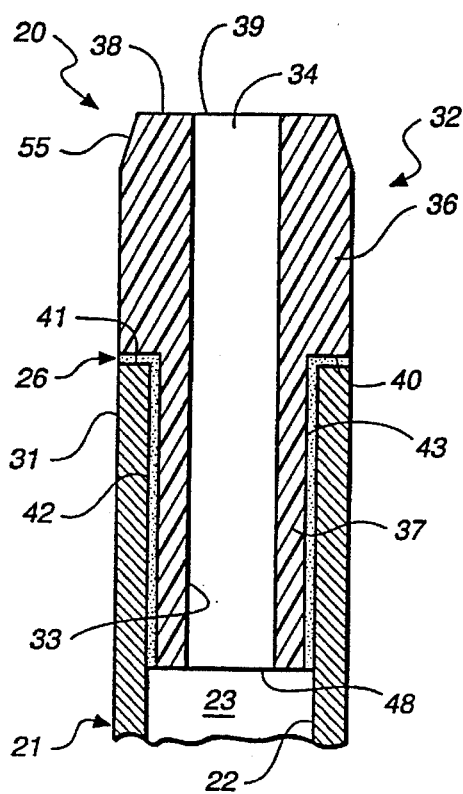
FIG._2
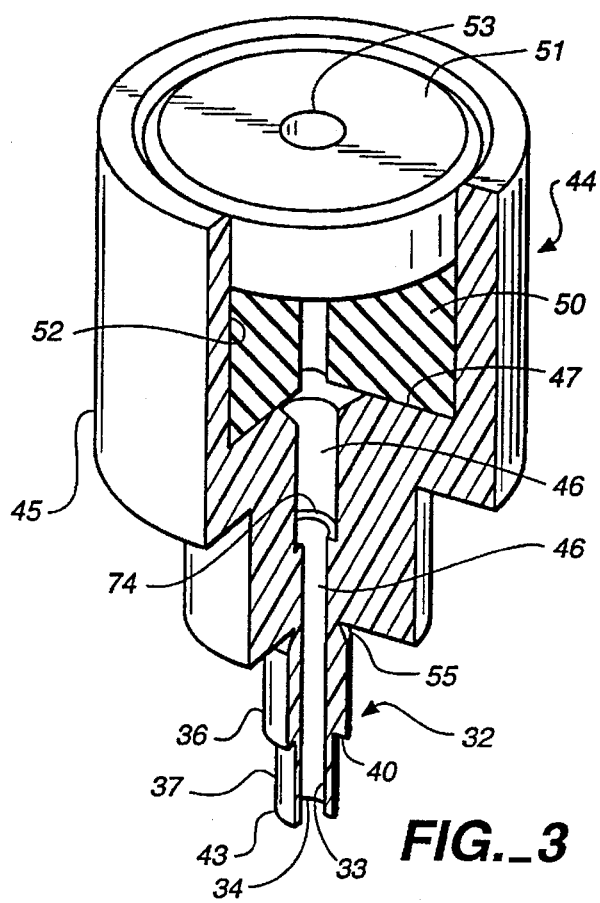
FIG._3
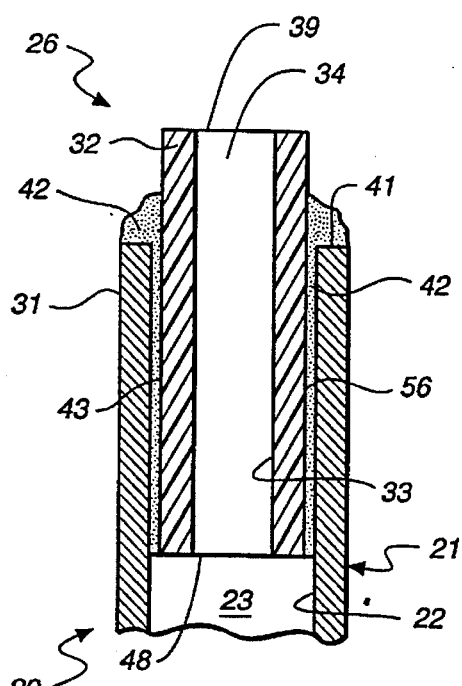
FIG._4A
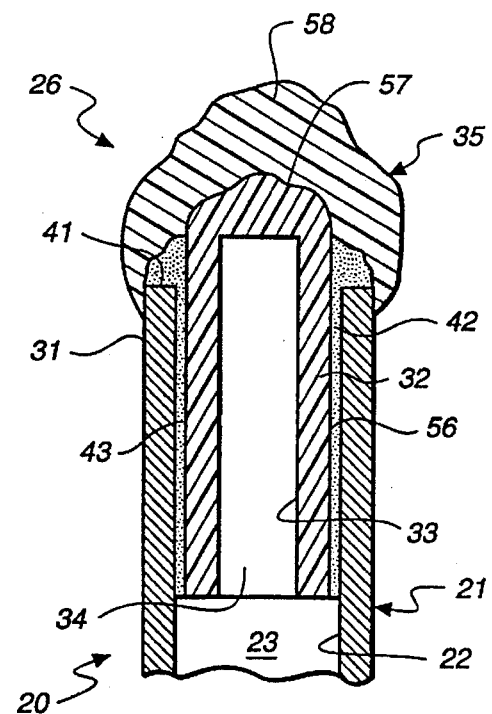
FIG._4B

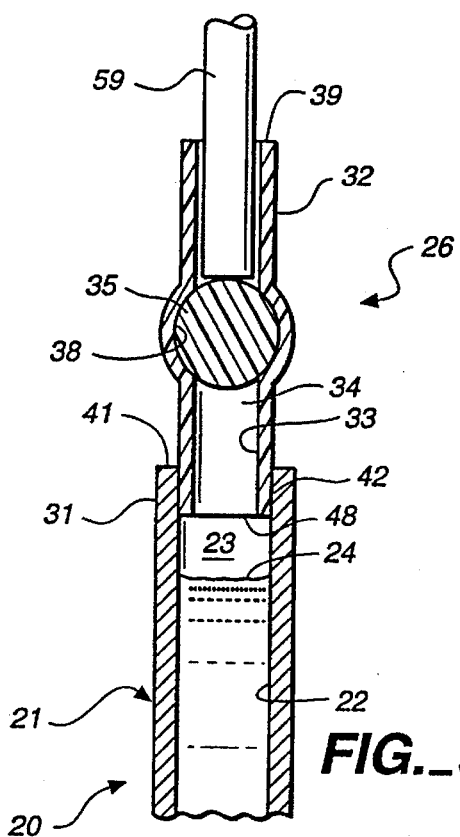
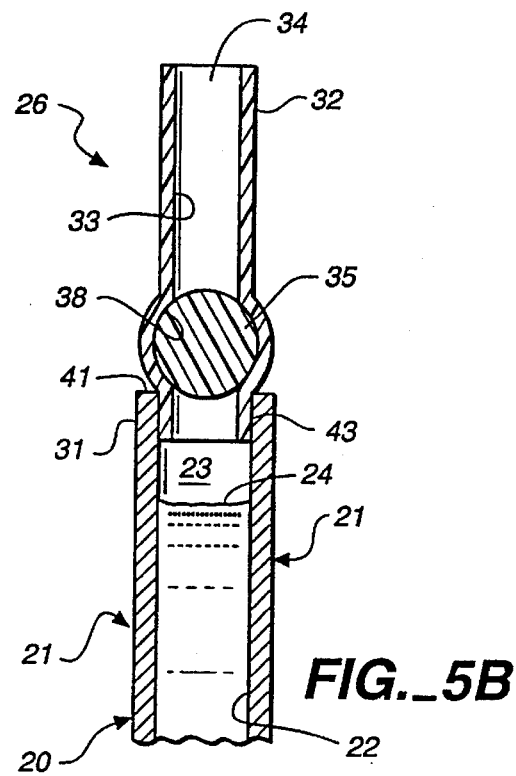
FIG._5A
FIG._5B
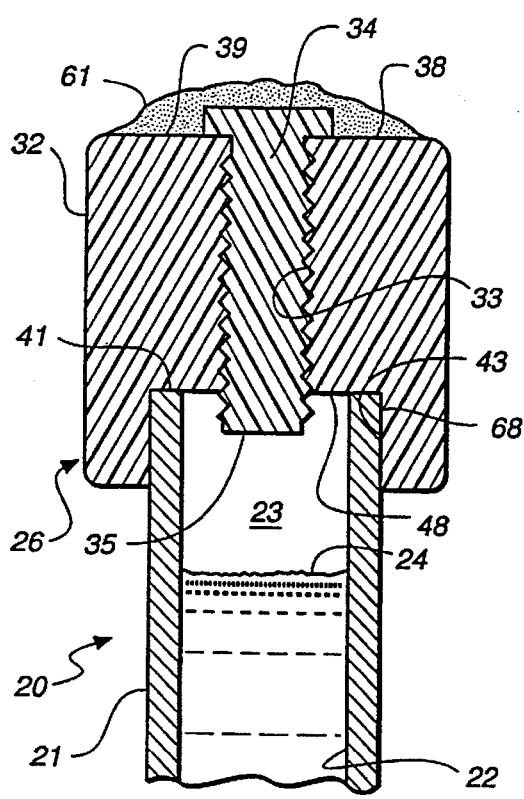
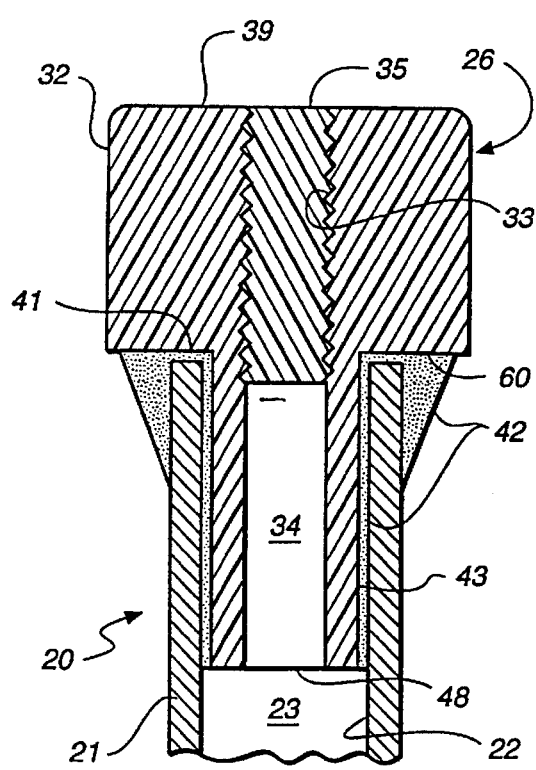
FIG._6
FIG._7

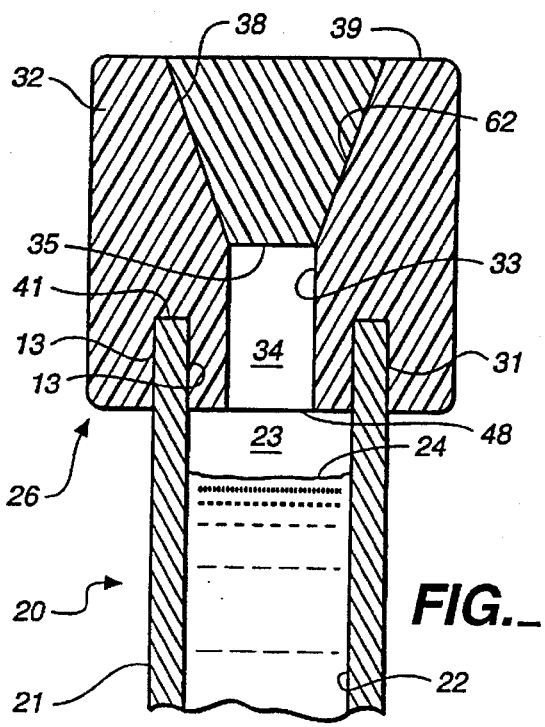
FIG._8
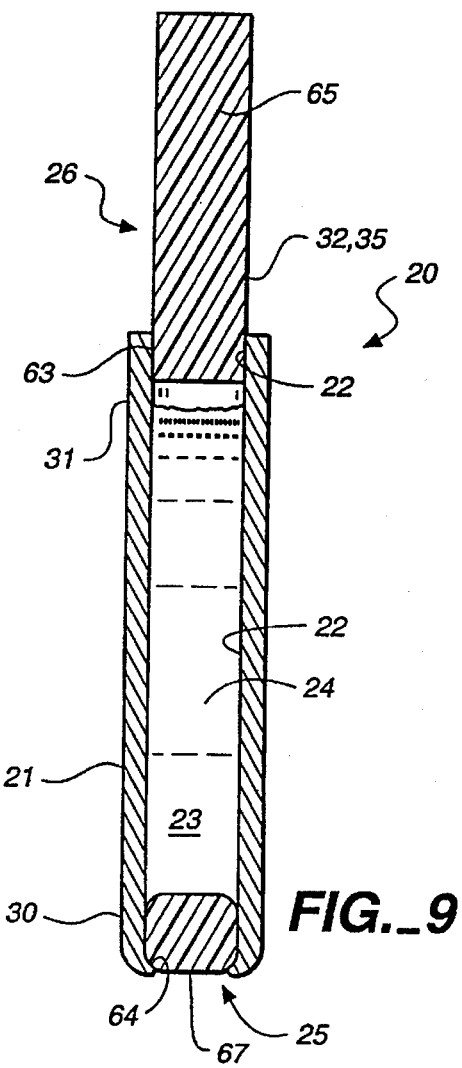
FIG._9
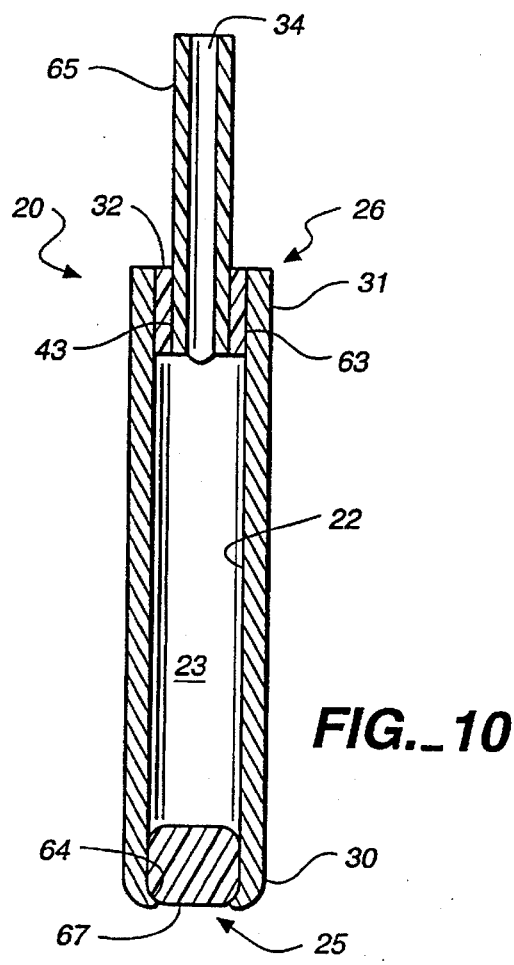
FIG._10
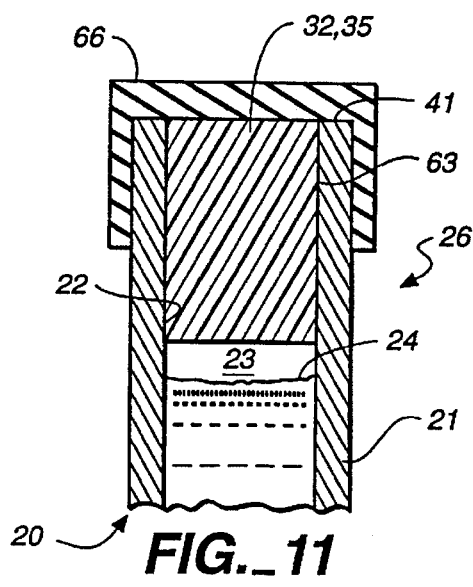
FIG._11

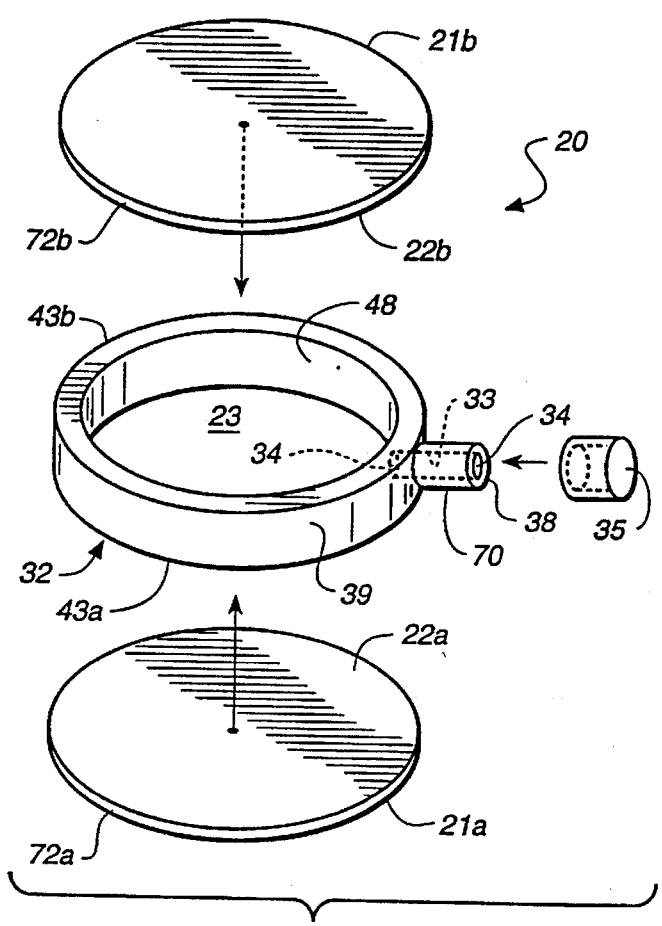
FIG._12
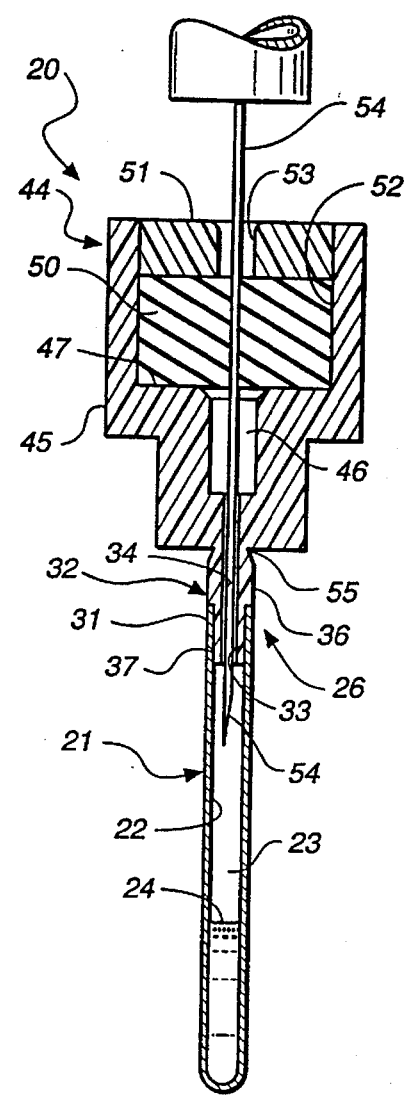
FIG._14
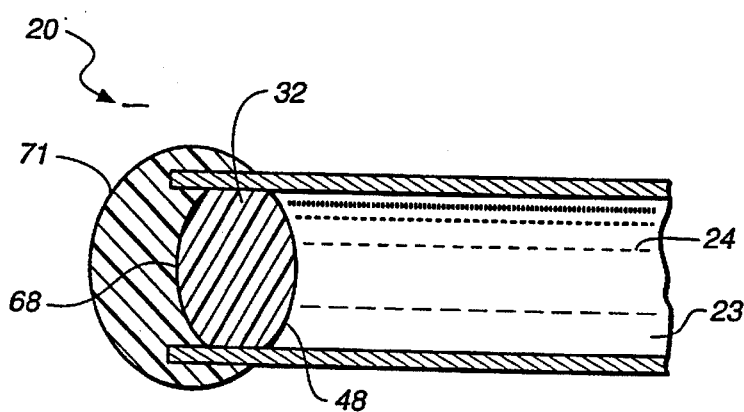
FIG._13

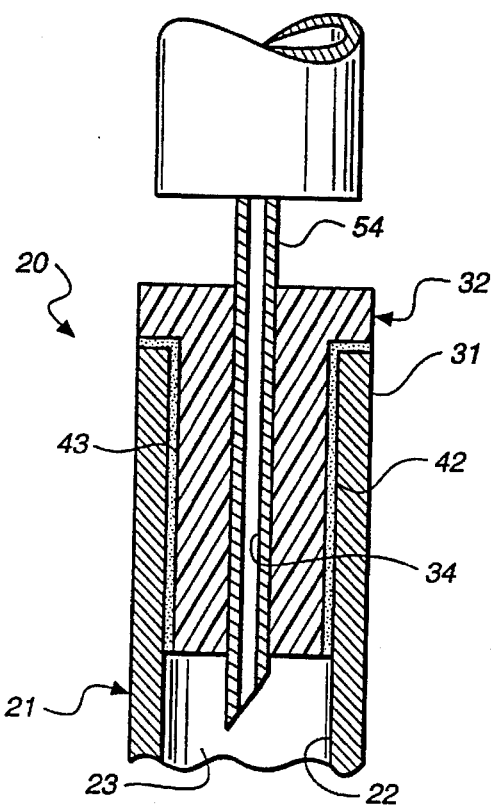
FIG._15
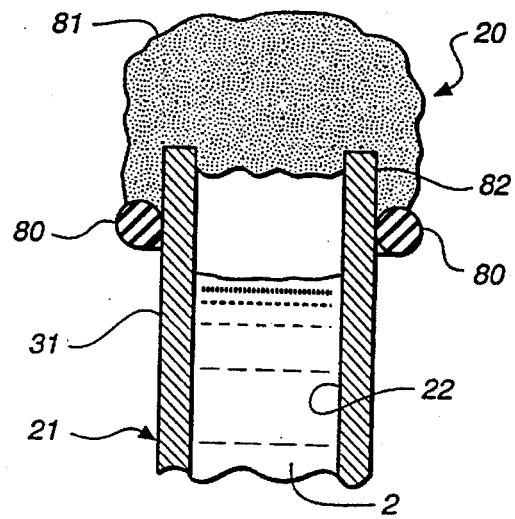
FIG._16
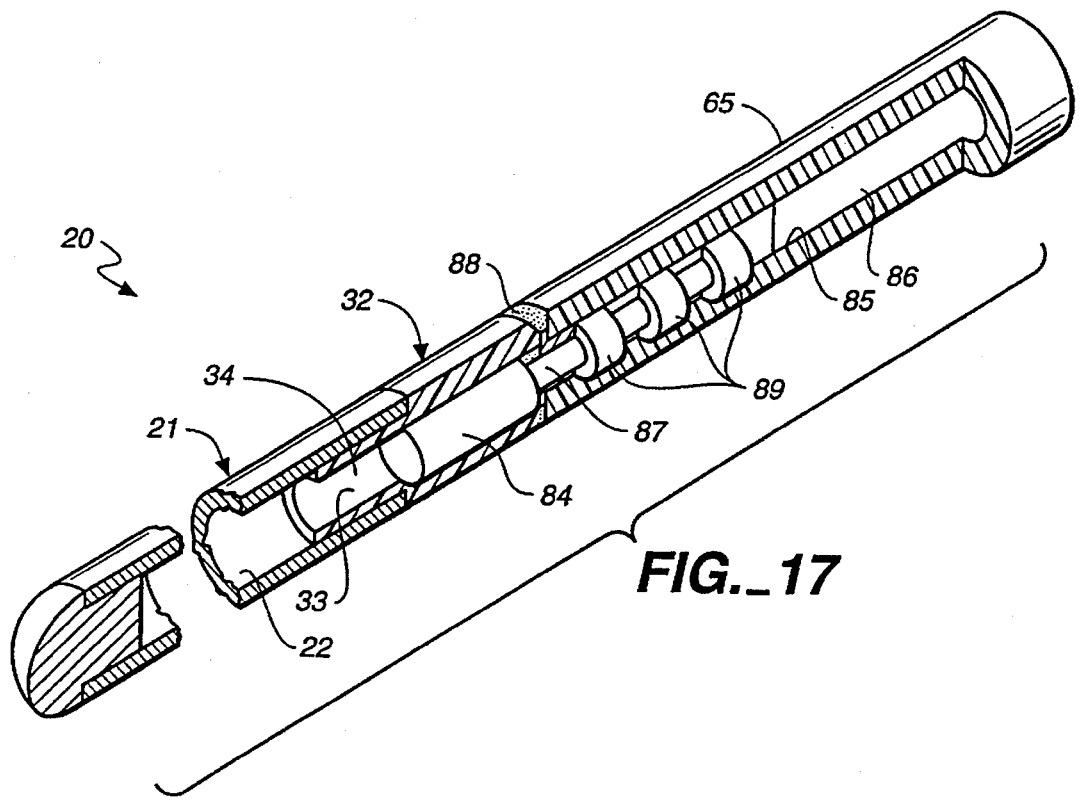
FIG._17

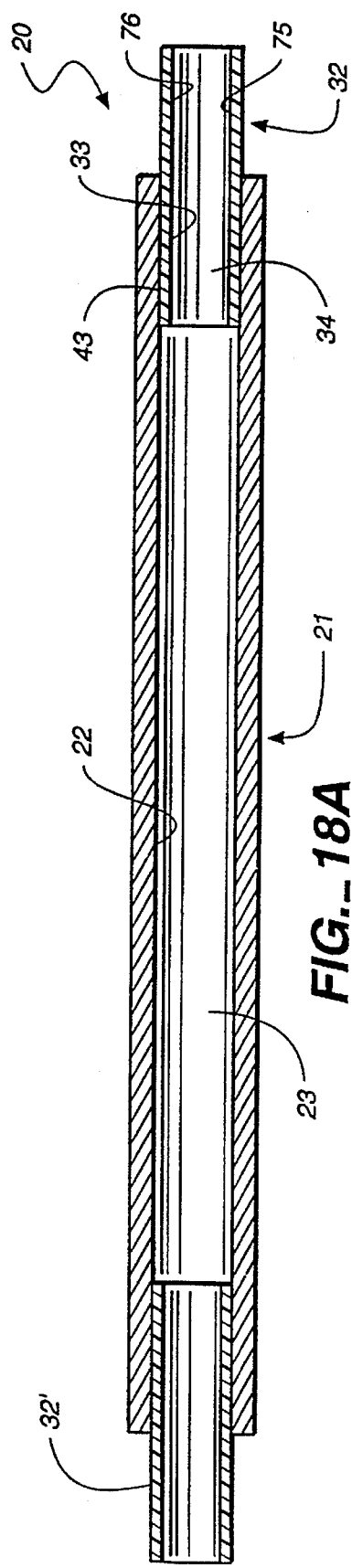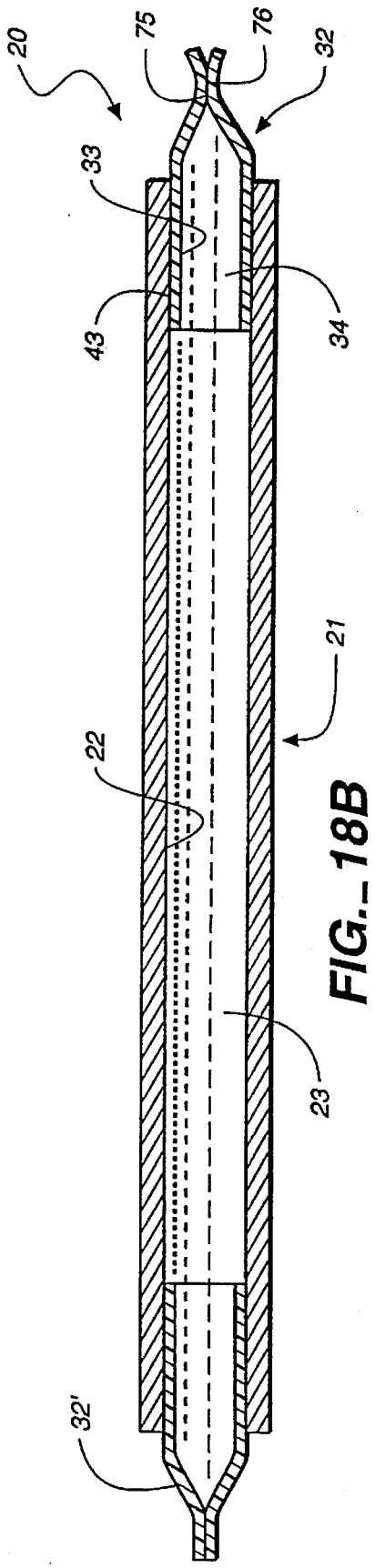

METHOD AND APPARATUS FOR SEALING IMPLANTABLE, MEMBRANE ENCAPSULATION

This is a division of the U.S. National application of Ser. No. PCT/U.S. 94/07015, filed Jun. 22, 1994, which is being filed concurrently herewith now abandoned; which is a continuation-in-part of application Ser. No. 08/082,407, filed Jun. 23, 1993, now abandoned.

TECHNICAL FIELD

The present invention relates, generally, to implantable, membrane encapsulation apparatus capable of infusing therapeutic agents and, more particularly, to methods and devices for sealing hollow membrane cell encapsulation apparatus.

BACKGROUND ART

The encapsulation of viable cells which produce biologically-active factors has experienced substantial growth and increased interest in recent years. These special implantable, encapsulating devices are capable of providing a vast array of biological functions and services. For example, biologically active therapeutic agents of living cells, such as enzymes, neurotransmitters, blood coagulation factors, lymphokines, cytokines, nerve growth factors, trophic factors such as neurotrophic factor, hormones and angiogenesis factors, may be continuously diffused into a host for therapeutic purposes. In other instances, these agents may be employed for diagnostic purposes. For example, the implanted cells could react to excrete some measurable product or the like in response to a particular physiological condition.

After considerable research, two general encapsulation approaches have evolved. One approach involves the manufacture of an encapsulating membrane around the viable cell cultures. Usually, microcapsules or microspheres, encapsulating a microscopic droplet of cell solution, are provided which are integral structures not generally requiring post-production sealing. This approach is disclosed in U.S. Pat. Nos.: 4,353,888 to Sefton and 4,352,833 to Lim; and European Patent No. 188,309 to Rha. One problem with these devices is that they are limited in volume, difficult to manufacture, implant and retrieve, and often suffer from limited biocompatibility.

Another encapsulation approach involves the use of macroencapsulation devices defining a cell suspension reservoir or lumen formed to hold the cell culture solution therein. These devices provide a much greater cell solution volume and are substantially easier to handle in both implantation and retrieval. One technique of fabricating a macroencapsulating device involves the coextrusion of an aqueous cell culture and a polymeric solution which forms a tubular extrudate having a polymeric outer coating encapsulating the viable cell solution. In some instances, the cell culture is fully encapsulated during the integral fabrication thereof, while in other instances, post-production sealing of the lumen is required. Example of these coextrusion devices may be found in U.S. Pat. No. 5,158,881 to Aebischer et al.

Another macrocapsule fabrication technique includes providing an elongated hollow fiber macroencapsulation structure which is subsequently loaded with the implantable cell cultures. In this approach, the hollow fiber macrocapsule is fabricated with one or more openings to the cell solution reservoir or lumen for cell loading, which subsequently must be sealed to fully encapsulate the cell cultures. Example of these devices may be found in U.S. Pat. No. 3,615,024 to Michaels.

Flatsheet encapsulation devices are also employed which generally include two flatsheet membranes encapsulating the cells therebetween to form an encapsulating sandwich. Both the cylindrical hollow fiber configuration and the flatsheet configuration provide a more favorable ratio (as compared to a sphere) between the surface area of the membrane and the volume of encapsulated tissue. In macrocapsules of these shapes, as the volume of the device is increased in order to contain greater amounts of encapsulated tissue, the corresponding surface area of the membrane increases more proportionately such that the diffusional transport of nutrients and products for increased amounts of tissue can be accommodated by increasing the surface area without unwieldy increases in total vehicle size.

These encapsulating membrane devices are generally comprised of thermoplastic polymer or copolymer membranes which exhibit characteristics of water insolubility and biocompatibility. This membrane material must be permselective to select therapeutic agents and cell nutrients, yet be impermeable to the cells producing those agents. Upon deposition or loading of the culture solution in the lumen of the hollow fiber, moisture infiltrates throughout the membrane and becomes trapped in the pores. Accordingly, the inner surface wall of the fiber defining the opening into the lumen becomes "wet" regardless of whether or not there has been direct contact with any of the aqueous cell solution. Hence, "wet" sealing techniques must be applied to seal the loading openings. The nature of the pores are such that moisture is drawn in by capillary action. In the case of narrow diameter fiber devices, capillary action within the fiber lumen further serves to distribute water and contaminants throughout the length of the fiber.

Traditional approaches to wet sealing thermoplastic encapsulation devices include the employment of polymer adhesives and/or crimping, knotting and heat sealing. Examples of these wet sealing techniques may be found in the following publications: J. Altman et al., "Successful Pancreatic Xenografts Using Semipermeable Membrane", 5 *Artificial Organs (Suppl.)* 776 (1981) (Polyvinylchloride acrylic XM50 copolymer tubing biocompatible epoxy or cyacrylate glue); J. Altman et al., "Long-Term Plasma Glucose Normalization in Experimental Diabetic Rats With Macroencapsulated Implants of Benign Human Insulinomas", 35 *Diabetes* 625, (1986) (poly(acrylonitrile-co-vinyl-chloride) (PAN/PVC) copolymer glue in solvent); B. Dupuy et al., "In Situ Polymerization of a Microencapsulating Medium Round Living Cells", 22 *J. Biomed. Materials Res.* 1061 (1988) (Photopolymerization of membranes around cells); W. Hymer et al., "Pituitary Hollow fiber Units In Vivo and In Vitro", 32 *Neuroendocrinology* 33 9 (1981) (PAN/PVC fibers syringe loaded, crimping with heated forceps); H. Iwata et al., "The Use of Photocrosslinkable Polyvinyl Alcohol in the Immunoisolation of Pancreatic Islets", 22 *Transplant Proceedings* 797 (April 1990) (Production of encapsulated cells using photocrosslinkable hydrogel); Y. Kojima et al., "Xenogeneic Pancreatic Islet Transplantation Using a Millipore Diffusion Chamber", 19 *Transplant Proceedings* 981 (February 1987) (Millipore MF cement); P. Lamberton et al., "Use of Semipermeable Polyurethane Hollow Fibers for Pituitary Organ Culture", 24 *In vitro Cellular & Developmental Biology* 500 (June 1988); C. Lum et al., "Intraperitoneal Nucleopore Chambers: a Murine Model for Allograft Rejection", 20 *Transplant Proceedings* 173 (April 1988) (Nucleopore membranes attached with silicone sealant; Millipore MF cement); S. Ronel et al., "Macroporous Hydrogel Membranes for a Hybrid Artificial Pancreas", 17 *J. Biomed. Materials Res.* 855 (1983)

(Pressure/heat sealing of hydrogel encapsulation devices); N. Theodorou et al., "Problems in the Use of Polycarbonate Diffusion Chambers for Syngeneic Pancreatic Islet Transplantation in Rats", 18 *Diabetologia* 313 (1980) (Polycarbonate filters sealed with polyacrylic cement); F. Wong et al., "Effects of Thymus enclosed in Millipore Diffusion Envelopes on Thymectomized Hamsters", 28 *Blood* 40 (1966); and G. Zondervan et al., "Design of a Polyurethane Membrane for the Encapsulation of Islets of Langerhans", 13 *Biomaterials* 136 (1992) (Polyurethane tubing sealed by knotting).

While these conventional methods of "wet" sealing may be adequate for laboratory experimentation or for short-term usage, their long term performance has often been inconsistent or unreliable. Potentially, these devices may be implanted in their host for months or years. Due to the nature of the fiber membrane material, to be discussed henceforth, the seal is often breached following implantation. This problem occurs on a consistent basis even when the method of sealing involves the same polymer solvent pair that was used to manufacture the encapsulating device.

Because of the porous nature of the membrane fiber material, moisture, cells, protein, polymers or the like contained in the cell culture solution become trapped in the pores of the membrane. As mentioned, the inner surface wall of the fiber defining the opening into the lumen becomes "wet" regardless of whether there is direct contact with the aqueous cell solution. Most common adhesives for this application, e.g., urethanes or thermoplastic adhesives, such as a PAN/PVC dissolved in the water-miscible solvent dimethylsulfoxide (DMSO), require relatively dry membranes to form a suitable seal and bond. In one instance, exposure to the moisture causes the thermoplastic adhesive to precipitate, thereby preventing adequate bonding to the wall of the fiber. In another instance, both protein and polymers present in the cell culture solution compete with the fiber present for gluing sites resulting in a contamination of the adhesive; thus preventing effective cross-linking in some areas. Hence, seal integrity is substantially degraded.

On the other hand, mechanical deformation (i.e., crimping or knotting), as well as heat sealing, tend to substantially weaken or crack the membrane over time. Due to the relative fragility of the membrane material, even a slight shearing force may fracture the membrane and render the device useless.

DISCLOSURE OF INVENTION

Accordingly, it is an object of the present invention to provide a method and apparatus for sealing implantable, hollow fiber encapsulation devices which maintain a longterm, cell-tight, seal integrity.

Another object of the present invention is to provide a method and apparatus for sealing loaded encapsulation devices which forms a reliable "dry" seal before and after cell loading.

Yet another object of the present invention is to provide a method and apparatus for sealing implantable, hollow fiber encapsulation devices which increases bonding of the adhesives to the fiber walls of the device.

It is another object of the present invention to provide a method and apparatus for sealing encapsulation devices without mechanically deforming the encapsulation device membrane surfaces.

Still another object of the present invention is to provide sealable entry ports for encapsulation devices, through which cell suspensions may be introduced into the device and subsequently reliably sealed.

It is a further object of the present invention to provide a method and apparatus for sealing implantable, encapsulation devices which is durable, compact, easy to maintain, has a minimum number of components and is economical to manufacture.

The present invention provides a sealed, implantable, encapsulation device for supplying a biologically active product or function to an individual. The encapsulation device comprises a fitting including an access port extending through the fitting from an outer surface to an inner surface. A permselective, porous, membrane having an interior surface cooperates with the fitting inner surface to define at least a substantial portion of a storage cavity therebetween. The membrane being in substantially cell-tight dry sealing engagement with an engaging surface of the fitting. Living cells are disposed in the storage cavity and are capable of secreting a biologically active product or of providing a selected biological function to an individual. The membrane is formed to permit passage of substances between the individual and cells required to provide the biological product or function. A plug member cooperates with a bonding surface of the fitting, proximate the access port, to form a cell-tight sealing engagement therewith to seal said access port.

In another aspect of the present invention, an encapsulation device comprises a first permselective, porous, sheet membrane having a first interior surface, and a second permselective, porous, sheet membrane spaced-apart from the first membrane and having a second interior surface oriented to face the first interior surface. A fitting is positioned between the first and the second membrane. The fitting is formed with an inner surface defining an access port extending through the fitting. The first membrane interior surface, the second membrane interior surface and the fitting inner surface cooperating to define a storage cavity therein. The first sheet membrane and the second sheet membrane both being mounted to respective engaging surfaces of the fitting in substantially cell-tight dry sealing engagement therebetween. A plug member cooperates with a bonding surface of the fitting to form a cell-tight sealing engagement therewith to seal the access port and the living cells disposed in the storage cavity.

In yet another aspect of the present invention, a method is disclosed for forming a sealed, implantable, hollow fiber membrane device for providing a biologically active product or function to an individual. The method comprising the steps of a) providing a permselective hollow, porous, membrane including an interior surface which defines a storage cavity and at least one open end into the cavity, and b) forming a cell-tight dry first seal at the open end of the membrane between the membrane and an engaging surface of a fitting. The fitting including an inner surface defining an open bore extending into the cavity. Next, c) the cavity is filled, through the open bore, with the living cell solution. The membrane permitting passage of substances between the individual and cells required to provide the biological product or function. After filling, d) a cell-tight second seal is formed at the fitting open bore by providing a plug member formed to cooperate with a bonding surface of the fitting to form a cell-tight sealing engagement therewith.

In another aspect of the present invention, an encapsulation device includes a generally flexible tubular fitting having a bonding surface and an abuttable surface. Upon the application of a solvent to both the bonding and the abuttable surfaces followed by the application of a washing fluid to the surfaces, these surfaces cooperate therebetween to form a cell-tight "wet" sealing engagement to seal the open bore upon contact of surfaces together. A method for forming this sealed, implantable, hollow membrane encapsulation device is also provided which includes: (a) providing a permselective hollow, porous, membrane; and (b) forming a cell-tight, first dry seal at the open end of the membrane between the membrane and an engaging surface of a flexible fitting 32. The method further provides: (c) filling or depositing in the cavity, through the open bore, living cells capable of secreting a biologically active product or of providing a selected biological function to an individual; and (d) forming a cell-tight second seal at the fitting open bore. This second seal is formed by: 1) exposing both the bonding surface and the abuttable surface to a solvent; 2) after the exposing step, washing the bonding surface and the abuttable surface with a washing fluid; and 3) after the washing step, contacting the bonding surface and the abuttable surface together to form the cell-tight second seal to seal the open bore.

BRIEF DESCRIPTION OF THE DRAWING

The assembly of the present invention has other objects and features of advantage which will be more readily apparent from the following description of the Best Mode of Carrying Out the Invention and the appended claims, when taken in conjunction with the accompanying drawings, in which:

FIGS. 1A–1C are a series of side elevation views, in cross-section, of a sealing implantable, hollow membrane encapsulation device constructed in accordance with the present invention having a detachable necked hub assembly and illustrating the filling and sealing of the encapsulation device.

FIG. 2 is an enlarged, fragmentary, side elevation view, in cross-section, of the membrane encapsulation device taken substantially along the bounded line 2—2 in FIG. 1B and showing an annular fitting mounted to an end of a hollow membrane.

FIG. 3 is an enlarged, top perspective view, partially broken away, of the necked hub assembly of FIG. 1A.

FIGS. 4A and 4B are a series of enlarged, fragmentary, side elevation views, in cross-section, of an alternative embodiment of the hollow fiber encapsulation device having a polyurethane tube fitting.

FIGS. 5A and 5B are a series of enlarged, fragmentary, side elevation views, in cross-section, of an alternative embodiment of the present invention having a deformable silicone tubing sealed by a ball shaped plug member.

FIG. 6 is an enlarged, fragmentary, side elevation view, in cross-section, of an alternative embodiment of the present invention illustrating a fitting molded to the end of the hollow membrane.

FIG. 7 is an enlarged, fragmentary, side elevation view, in cross-section, of another alternative embodiment of the encapsulating device employing a threaded allen screw as a plug member.

FIG. 8 is an enlarged, fragmentary, side elevation view, in cross-section, of yet another alternative embodiment of the present invention employing a conical plug member.

FIG. 9 is an enlarged, side elevation view, in cross-section, of still another alternative embodiment of the hollow membrane encapsulation device employing a polymeric elasticity memory material fitting.

FIG. 10 is an enlarged, side elevation view, in cross-section, of another alternative embodiment of the polymeric elasticity memory material fitting having a tubular tether portion.

FIG. 11 is an enlarged, side elevation view, in cross-section, of another alternative embodiment of the polymeric elasticity memory material fitting having a memory material cap member.

FIG. 12 is an exploded top perspective view of a flat sheet encapsulation device constructed in accordance with the present invention.

FIG. 13 is an enlarged, fragmentary, side elevation view, in cross-section, of the flat sheet encapsulation device of FIG. 12 and illustrating a molded edge.

FIG. 14 is a side elevation view, in cross-section, of a cup-shaped hollow membrane encapsulation device of the present invention having a detachable necked hub assembly and illustrating the filling of the device with a hypodermic syringe needle.

FIG. 15 is an enlarged, fragmentary, side elevation view, in cross-section, of a hollow membrane encapsulation device of the present invention having a self-sealable fitting and illustrating the filling of the device with a hypodermic syringe needle.

FIG. 16 is an enlarged, fragmentary, side elevation view, in cross-section, of a hollow membrane encapsulation device of the present invention having a fitting formed of adhesive which bonds to a cured bead of adhesive cell-tight "dry" sealed to the membrane.

FIG. 17 is a top perspective view, partially broken away, of an encapsulation device of the present invention having a tether connector for mounting the tubular tether portion to the hub.

FIGS. 18A and 18B are a series of side elevation views, in cross-section, of a hollow membrane encapsulation device of the present invention having flexible fittings each having opposed surfaces formed to bond to one another in a cell-tight sealed engagement.

BEST MODE OF CARRYING OUT THE INVENTION

The following description is presented to enable a person skilled in the art to make and use the invention, and is provided in the context of a particular application and its requirements. Various modifications to the preferred embodiment will be readily apparent to those skilled in the art, and the generic principles defined herein may be applied to other embodiments and applications without departing from the spirit and scope of the invention. Thus, the present invention is not intended to be limited to the embodiments shown, but is to be accorded with the widest scope consistent with the principles and features disclosed herein. It will be noted here that for a better understanding, like components are designated by like reference numerals throughout the various figures.

Attention is now directed to FIGS. 1(A–C) and FIG. 12, where the subject sealed, implantable, encapsulation device, generally designated 20, for diffusing a biologically active product or function to an individual is illustrated. Briefly, the present device includes a fitting, generally designated 32, having an access port or open bore 34 extending through fitting 32 from an outer surface 39 of the fitting to an inner surface 48 of the fitting. A permselective, porous, membrane, generally designated 21, having an interior surface 22, cooperates with the fitting inner surface to form at least a substantial portion of a storage cavity or lumen, generally designated 23, therebetween. That is, fitting inner surface 48 and membrane interior surface 22 together define a substantial portion or all of storage cavity 23. In accordance with the present invention, membrane 21 is in substantially cell-tight dry sealing engagement with an engaging surface 43 of fitting 32 to seal cavity 23. Living cells in cell culture solution 24 are disposed in the cavity which are capable of secreting a biologically active product or of providing a selected biological function to an individual. Further, membrane 21 is formed to permit passage of substances between the individual and cells required to provide the biological product or function. A plug member, generally designated 35, cooperates with a bonding surface 38 of the fitting to form a cell-tight sealing engagement therewith to seal open bore or access 34.

In one particular configuration of the present invention (FIGS. 1–11), the permselective hollow membrane substantially defines storage cavity or a lumen 23 therein in which the living cells in cell culture solution 24 are disposed. First and second sealing means 25 and 26, respectively, are provided at respective first and second ends 30 and 31, respectively, of membrane 21 to form a cell-tight lumen 23 therein. Second sealing means 26 includes fitting 32 having inwardly facing surface 33 which defines open bore 34. As mentioned, an engaging surface 43 of fitting 32 is formed and dimensioned to be in a cell-tight, dry sealing engagement with membrane end 31. Plug member 35 cooperates with a bonding surface (fitting distal end bonding surface 38 and/or fitting inwardly facing surface 33) of the fitting to form a cell-tight sealing engagement therewith to seal open bore 34.

In another particular configuration of the present invention (FIGS. 12 and 13), a flat sheet encapsulation device 20 is provided including a first permselective, porous, sheet membrane, generally designated 21a, having a first interior surface 22a, and a second permselective, porous, sheet membrane, generally designated 21b, spaced-apart from the first membrane and having a second interior surface 22b oriented in opposed relation to the first interior surface 22a. Fitting 32 is positioned between the first and second membrane (FIG. 12) and is formed with inwardly facing surface 33 which defines access port 34 extending through the fitting. First membrane interior surface 22a, second membrane interior surface 22b and the fitting inner surface 48 cooperate to form storage cavity 23 which holds living cell solution 24 therein. The first interior surface 22a and the second interior surface 22b further both being mounted to the fitting in substantially cell-tight dry sealing engagement therebetween. Plug member 35 cooperates with bonding surface 38 of the fitting to form a cell-tight sealing engagement therewith to seal the access port and the living cells disposed in the storage cavity.

In accordance with the present invention, before cell culture solution 24 may be filled into the lumen or storage cavity of either particular configuration, a reliable, cell-tight, "dry" seal is formed between fitting 32 and the porous, permselective membrane 21. First, the seal is "cell-tight" which means that the seal is impermeable to the viable cells contained in the solution, similar to fiber membrane 21, so that they will not pass therethrough and into the host. Yet, the seal may be permeable to the other cell solution constituents, such as nutrients, therapeutic agents or the like. Secondly, it will be understood that the term "dry" seal is defined as a seal formed between a substantially moisture or water-free membrane and the substantially annular fitting 32 of the second sealing means 26. Since this "dry" seal technique is employed before potential contamination by the cell solution, it is considerably more reliable than the "wet" sell techniques. A dry semipermeable membrane is afforded the opportunity to suitably bond to a dry surface of the fitting.

Accordingly, the absence of moisture or water in the pores of the membrane, caused by contact with the solution, substantially reduces seal failure, e.g., precipitation of the adhesives employed. Further, the absence of cell solution elements decreases contamination of the adhesive so that it may effectively bond between the opposing adhesive sites surfaces.

This can be contrasted to the "wet" seal technique employed in most of the prior art fiber devices after the lumen has been filled or loaded with the viable cell solution. As mentioned, one of the problems associated with the prior art implantable, hollow fiber devices is their inability to form reliable seals with or bond to a "wet" membrane surface at the open end thereof due to contamination by the cell solution.

Subsequently, as shown in FIG. 1A for example, the cell culture solution may be disposed or deposited, through open bore 34 in fitting 32, in a manner to be discussed in greater detail below. Since the annular fitting is substantially non-porous, it will not have the tendency to absorb or trap the well solution thereupon. Even should the solution contact the bonding surface 38 or inwardly facing bonding surface 33 of the fitting, the solution can be easily removed in a suitable manner. For instance, a volatile, biocompatible solvent may be applied on a swab to wipe the fitting surface so that the surface becomes "dry" or free of the above-mentioned contaminants. When plug member 35 is bonded or attached to the top surface or inwardly facing surface 33 of fitting 32 (FIG. 1C), another suitable "dry" bond may be attained which, again, is not subject to the bonding deficiencies experienced by the prior art assemblies.

Accordingly, the novel technique and structure of the present invention permits "dry" bonding of the membrane to a fitting to form substantially cell-tight seals. This seal and bond, hence, remains integral for months or years after implantation in its host. Importantly, this technique is substantially non-toxic to the cells and will not effect their viability. The present invention, further, does not mechanically deform either the fragile membrane or the fitting to cause fatigue or stress. Moreover, as will be more apparent, the cell-tight "dry" seal may be formed through mechanical contact between the fitting and the membrane and/or through a suitable adhesive.

Referring back to FIGS. 1–11, the first particular configuration of the present invention will now be described in greater detail. Hollow membrane 21 and first sealing means 25, which preferably provides no passages into lumen 23, are conventional structures well known in the field. First sealing means 25 may be formed at one end 30 of the hollow membrane in any traditional manner applied in the art (i.e., polymer adhesives, and/or crimping, knotting and heat sealing). Hence, the manner in which both hollow membrane 21 and first seal 25 are formed do not constitute a novel feature of the present invention and are not claimed as such. However, it will be understood that first open end 30 of hollow fiber membrane 21 may be cell-tight dry sealed employing the fittings and the same techniques which cell-tight dry seal second open end 31. It will further be understood that hollow membrane 21 may be provided with only one open end 31, as best viewed in FIG. 14, extending into storage cavity 23. In this arrangement, hollow membrane 21 is cup-shaped and only open end 31 need be sealed. These cup-shaped membranes may be formed using a capsule extrusion method disclosed in our PCT Application, S.N. W09300063.

As illustrated in FIG. 2, annular fitting 32 includes a base portion 36 projecting outwardly from membrane second end 31 and a leg portion 37 extending downwardly from base 36. The outer perimeter of leg portion 37 is formed and dimensioned to be received in lumen opening at second or opposing end 31. Upon receipt, a downwardly facing shoulder portion 40 of the fitting, formed by the intersection between base 36 and leg portion 37, seats against an upper annular edge 41 of second end 31. In this configuration, annular fitting 32 is preferably substantially rigid and may be composed of one of a number of suitable biocompatable materials which are substantially non-toxic to the living cells. These materials include polyurethanes, epoxies, silicones, and acrylate polymers like alkaline methoacrylates, cyano acrylates, polymethyl methacrylate and poly((2-dimethylamino)ethyl methacrylate.

In a preferred form, an adhesive 42 (FIG. 2) is provided which forms the suitable above-defined "dry" seal and bond between the outer circumferential engaging surface 43 of leg portion 37 and the interior surface 22 of porous membrane 21. The adhesive must be a substantially rapidly polymerizing adhesive, to reduce potential toxic contamination of the cells by uncured adhesive, and must not discharge sufficient toxic by-products to be substantially detrimental to cell viability. Hence, the adhesive must also substantially polymerize completely. Suitable adhesives include light-curable acrylate polymer adhesive, two-part polyurethane adhesives, epoxies, silicones, and other acrylate polymers. In some instances, the adhesive could be polymerized in situ therewith, as opposed to precipitated, to form an effective, durable polymer bond with the fitting.

After fitting 32 has been "dry" sealed to membrane 21, the encapsulation device may be sterilized by any conventional method which does not degrade the integrity of the membrane, such as ethylene oxide (ETO).

Referring back to FIGS. 1A–1C, one preferred embodiment of the present invention is illustrated including a detachable necked hub assembly, generally designated 44, coupled to base 36 of the annular fitting by a frangible neck portion 55. Therefore, the hub assembly is capable of selective separation from the fitting upon breaking of the frangible neck portion 55 at a frangible region thereof.

As best viewed in FIG. 3, hub assembly 44 includes a housing 45 which provides a passageway 46 positioned in axial alignment with open bore 34 of annular fitting 32. Hence, while annular fitting 32 is "dry" sealed to membrane 21, the lumen may be accessed through passageway 46 and open bore 34.

Passageway 46 includes a cavity portion 47 formed and dimensioned to receive and seat a seal member 50 therein. As will be discussed below, seal member 50 provides an access hole 49 extending therethrough, in coaxial alignment with passageway 46, which is formed to permit the passage of a filling tube 54 (FIG. 1A) therethrough for deposition of cell solution 24 into storage cavity 23. A cap member 51 is provided to be positioned over seal member 50 which is snap fit or snugly engaged with the vertical walls 52 forming cavity 47 to snugly retain the cap member in cavity 47. Seal 50, preferably silicone, will then be stably retained in cavity 47. Cap member 51 includes a port 53 extending therethrough which permits access to seal member access hole 49 and to passageway 46.

Housing 45 may be integrally formed with fitting 32 and may be fabricated using conventional machining or molding techniques. This housing may be composed of an acrylate polymer or the like.

In accordance with the present invention, as viewed in FIG. 1A, seal member 50 may be pierced by inserting filling tube 54 through port 53 and forcing it through seal member access hole 49, and thereon through passageway 46 until a distal end 73 of filling tube 54 abuts against an upwardly facing shoulder portion 74 of housing 45. This shoulder portion prevents the substantially blunt distal end 73 of filler tube 54 from penetrating open bore 34 and extending into cavity 23 where the filling tube distal end may cause damage to the membrane. Shoulder portion 74, as shown in FIGS. 1 and 3, is formed from the intersection of passageway 46 and the smaller diameter open bore 34. Accordingly, the outer diameter of filling tube 54 is larger than the diameter of open bore 34 and smaller than the diameter of passageway 46.

Seal member 50 is preferably composed of a resilient flexible material, such as silicone, which will permit a larger diameter filling tube 54 to be passed through smaller diameter access hole 49. The resiliency of seal member 50 creates a seal around the outer periphery of filling tube 54 sufficient to prevent contaminants from entering storage cavity 23 during filling thereof.

Subsequently, cell suspension 24 may be filled, injected or deposited into lumen 23 through filling tube 54 to a level just below the bottom of leg portion 37 of the fitting. Incidently, due to the porous nature of membrane 21, the volume of air already inside cavity 23 is displaced through the pores during filling. Further, the cell suspension fluid or water also flows out of the pores which essentially concentrates the cell solution in the cavity.

The filling tube is then withdrawn, whereupon, the necked hub assembly may be selectably and manually separated from annular fitting 32 (FIG. 1B). FIGS. 1A, 2 and 3 illustrate that neck portion 55 is inwardly inclined which facilitates selective separation of the hub assembly from the fitting by manually applying a shearing force thereto. Upon breaking the frangible neck portion 55 (FIG. 1B) and separating the hub assembly 44, a virgin bonding surface 38 and the end of open bore 34 is exposed which subsequently must be sealed.

Exposed open bore 34 of the annular fitting may be closed or sealed using a light curable acrylate adhesive (e.g., Luxtrak™ LCM adhesives by ICI Resins U.S.) or other biocompatible adhesive to form plug member 35 which cooperates with fitting distal end bonding surface 38 or inwardly facing surface 33 to form a cell-tight sealing engagement therewith to seal the open bore. In the light curable approach, a blue light may be employed which is not damaging to the viability of the cells.

The virgin portion of the bonding surface, which is created by the fracture of the neck portion, is sufficiently rough or jagged to enhance bonding of the adhesive thereto. Hence, as viewed in FIG. 1C, an open bore seal plug member 35 of adhesive that covers open bore 34 is more securely bonded to bonding surface 38 in a manner forming another cell-tight, "dry" seal.

The hub assembly 44 may be removed without causing the cell solution to wet or contaminate inwardly facing surface 33 of open bore 34. However, should the solution wet the inwardly facing surface, it may be removed in most instances, as discussed above, so that it becomes "dry". Furthermore, it will be appreciated that the lumen may be filled by any conventional method which substantially prevents the cell solution from contacting inwardly facing surface 33 forming open bore 34 to which a "dry" seal is to be formed. For example, in an alternative approach, the filling tube may be provided by a hypodermic syringe needle 54, as shown in FIG. 14, which pierces seal member or septum 50 by inserting syringe needle 54 through port 53, piercing septum 50, and thereon through passageway 46 and open bore 34 proximate lumen 23. Subsequently, cell suspension 24 may be filled, injected or deposited into lumen 23 through syringe needle 54 to a level just below the bottom of leg portion 37 of the fitting. It will further be appreciated that other filling methods, such as commercially available automated techniques, may be employed as well.

In a related embodiment, fitting 32 may be composed of a resilient self-sealable material, such as silicone, which is formed and dimensioned to be positioned in second open end 31 in a manner causing a cell-tight "dry" seal between fitting 32 and the porous, permselective membrane 21. In this configuration, as best viewed in FIG. 15, fitting 32 provides no access port into storage cavity 23. Hence, fitting 32 must be capable of permitting passage of a syringe needle or the like so that the syringe forcibly creates an access port 34. In accordance with the present invention, after the living cells are deposited in the storage cavity and upon withdrawal of the needle therefrom, the self-sealable fitting 32 is sufficiently resilient to sealably close access port 34 caused by the syringe to form a cell-tight seal.

Turning now to FIGS. 4A and 4B, an alternative embodiment of the present invention is illustrated. Rather than the annular fitting being substantially preformed and/or molded, the fitting 32 may merely be comprised of a section of tubing having an outer perimeter engaging surface 56 which is "dry" sealed to the interior surface 22 by adhesive 42. Preferably, tubular fitting 32 is provided by polyurethane tubing which projects distally beyond the annular edge portion 41 of the membrane 21. Similarly, adhesive 42 may be a two-part polyurethane adhesive (e.g., CasChem 2-part Vorite/Polycin Adhesive).

FIG. 4A shows that tubular fitting 32 is provided with open bore 34 for the injection of the cell suspension by a filler tube (not shown) or the like. Upon removal of the tube, open bore 34 is preferably sealed by melting the upper portion of the tubing extending beyond the hollow membrane to form melted seal plug member 57 (FIG. 4B). Since polyurethane fuses quickly and is a poor heat conductor, the process of heating the upper portion the end with a soldering iron or the like will not significantly heat the cells and thus will not effect their viability. As a precautionary measure, the fused upper seal 57 of tubular fitting 32 may be covered with an acrylate polymer seal 58 (FIG. 4B) or the like to ensure a cell-tight, "dry" seal. Accordingly, in this configuration, both fused seal 57 and polymer seal 58 form plug member 35.

Tubular fitting 32 could further be comprised of a deformable, substantially non-porous material such as silicone. In this embodiment, as best viewed in FIGS. 5A and 5B, open bore 34 may be sealed by pushing a stainless steel, teflon or other polymer ball-shaped plug member 35, via rod 59, into open bore 34 of tubular fitting 32. The diameter of ball-shaped plug member 35 is preferably provided with a larger diameter than the inner diameter of both open bore 34 and lumen 23. In this manner, as rod 59 pushes plug member 35 into tubular fitting 32, the ball resiliently expands inwardly facing surface 33 of the fitting to form a suitable cell-tight seal. Plug member 35 is preferably pushed all the way down until it is positioned proximate the annular edge portion 41 of membrane 21 (FIG. 5B). An adhesive (not shown) may then be applied into bore 34 to retain the ball-shaped plug member 35 in place.

In another embodiment of the present invention, as best viewed in FIG. 6, the inwardly facing surface 33 forming open bore 34 of annular fitting 32 may be threaded. To seal the bore, a threaded plug member 35 or screw may be provided which engages the threads. Similarly, an acrylate polymer seal 61 or the like may cover the head of screw plug member 35 to ensure a cell-tight, "dry" seal and, further, provide a smoother overall top surface.

This embodiment may be fabricated by attaching a prefabricated threaded port to the end of the membrane or by molding a fitting directly to the membrane end. In this arrangement, no adhesives will be necessary since fitting 32 is molded directly thereto. The molded fitting preferably comprises a substantially non-porous polyurethane or the like. The embodiment of FIG. 6 further illustrates that engaging surface 43 may cooperate with an outer facing peripheral surface 68 of membrane 21 to form a substantially cell-tight "dry" sealing engagement therewith.

FIG. 7 shows that the threaded plug member may be provided by a headless screw such as an allen screw plug 35 in order to lie flush with the upper surface of the fitting so that it may be smooth. The fitting 32 in this embodiment may extend past annular edge portion 41 of the hollow membrane 21 to form a ledge 60 to retain additional adhesive sealant 42. This further ensures a proper "dry" seal between the non-porous fitting and the porous fiber membrane.

In yet another alternative embodiment, open bore 34 may include a tapered portion 62 (FIG. 8) which inclined outwardly which is formed and dimensioned to receive a conical plug member 35 Of a suitable material, such as a polymer or an elastomer. Conical plug member 35 may be friction fit in tapered bore portion 62 or may be bonded thereto by applying the above-mentioned adhesives. When adhesives are applied in this application, it will be appreciated that the material of plug member 35 be substantially non-porous which facilitates adhesion of plug member 35 thereto. Moreover, it will be understood that the plug member 35 and similarly shaped bore portion 62 may be practically any convenient geometric shape without departing from the true scope and nature of the present invention. Alternatively, tapered portion 62 may be sealed with a suitable adhesive.

As best viewed in FIG. 9, fitting 32 may be formed from a polymeric elasticity memory material capable of controlled and predetermined expansion and/or contraction above and below a glass transition region temperature, $T_g$. In a polymeric elasticity memory material, such as that disclosed in Y. Shirai et al., "Development of Polymeric Shape Memory Material", *Mitsubishi Technical Bulletin* n.184 (December 1988), the material may exhibit and retain certain structural and physical properties at a temperature above $T_g$ as compared to those properties while at $T_g$. Similarly, the material may exhibit and retain certain structural and physical properties at a temperature below $T_g$ as compared to those properties at $T_g$ and above $T_g$.

For example, in accordance with the present invention, the memory material composing fitting 32 (FIG. 9) may exhibit a reduced modulus of elasticity, at a temperature above and below $T_g$, as compared to its modulus of elasticity at $T_g$. Hence, fitting 32 may be fabricated to a desired shape and transverse cross-sectional area (not shown), at body temperature (i.e., 98.6° F. which the material will retain once device 20 is implanted in the body), which is greater than the transverse cross-sectional area (not shown) defined by the interior surface 22, at second end 31. Subsequently, fitting 32 may be cooled to its $T_g$, preferably between the body temperature and room temperature, where the fitting may be deformed and reshaped to have a transverse cross-sectional area less than that enclosed by the interior surface at second end 31. This smaller area will facilitate insertion into the lumen entrance. By further cooling the material below $T_g$, because the modulus of elasticity is reduced at a temperature below and above $T_g$, deformed fitting 32 will retain its shape until rewarmed back up to $T_g$. Upon insertion into this entrance of lumen 23, and upon rewarming of the fitting back to $T_g$, the fitting will convert back to its structural shape and physical characteristics exhibited at a temperature above $T_g$. Therefore, upon expansion of the transverse cross-sectional area of the fitting, the perimeter wall 63 will engage or force-fit in sealing contact against interior surface 22 of lumen 23 to form a suitable cell-tight, dry seal therebetween. Further, by maintaining the material at body temperature, the shape and physical characteristics of the material will be retained as well. In this way, the fitting 32 of elasticity memory material expands to serve as a plug member 35, forming a cell-tight seal between the interior surface 22 of the lumen 23 and the perimeter wall 63. A similar type of fitting 32, expanded to form a plug member 35, is also shown in FIG. 11.

It will be appreciated that first sealing means 25 may also be composed of a elasticity memory material. In this form, it may be preferable to provide an annular seating portion 64 proximate the bottom opening of first end 30 having a transverse cross-sectional area smaller than that of the lumen. A memory material fitting 67 of first seal 25 may then be inserted into lumen 23 and seated against seating portion 64 proximate first end 30. Subsequently, the material may be rewarmed to $T_g$ where the diameter expands so that the outer perimeter wall 63 is in force-fit sealing contact against interior surface 22 of lumen 23 to form a suitable cell-tight, dry seal therebetween.

Because of the reduced modulus of elasticity upon rewarming the material to body temperature, as compared to the modulus at $T_g$, the memory material may be used to form a tether portion 65 which functions to anchor encapsulation device 20 with the recipient. Hence, the tether may be attached to the appropriate area of the recipient with a suture, surgical staple or the like. Further, tether 65 may aid in the removal of the membrane encapsulation device from the body.

FIG. 10 illustrates that the memory material fitting 32 may also work in conjunction with a .substantially non-porous tubular tether device 65 which cofunctions as a tether and a means for loading the lumen with cell solution (not shown) through open bore 34. In this arrangement, open bore 34 may be cell-tight sealed by a plug member (not shown) composed of a memory material or may be sealed by the above-mentioned methods so as to form a "dry" seal.

Finally, as best viewed in FIG. 11, a polymeric elasticity memory, cup-shaped, end cap 66 may be provided which exhibits the structural and physical characteristics in which, rather than expanding at a temperature above $T_g$, the cap 66 contracts or shrinks at $T_g$ and at body temperature to sandwich membrane 21 between cap 66 and memory material fitting 32, thereby forming a cell-tight seal therebetween.

Turning now to FIGS. 12 and 13, the substantially flat encapsulation device configuration of the present invention will now be described. In the preferred form of flat sheet device 20, fitting 32 is provided by a relatively thin annular ring member having an inner diameter formed by inner surface 48. Inwardly facing surface 33 forms access port 34 extending into storage cavity 23 so that cavity 23 may be filled with living cell solution 24. Device 20 is thus a substantially flat disc-shaped encapsulation device.

It will be understood, however, annular ring fitting 32 may be formed in many other practical geometric shapes as well without departing from the true spirit and nature of the present invention. The main principal is that fitting inner surface 48 is formed to cooperate with the interior surfaces 22a, 22b of sheet membranes 21a, 21b, respectively, to form storage cavity 23. For instance, fitting 32 may be shaped as a half-annular ring (not shown) or be wedge-shaped. This configuration may necessitate either: bonding engagement between sheet membranes 21a and 21b in a cell-tight dry sealing manner; or providing a single sheet membrane which extends around the ring to cell-tight dry seal with both a first engaging surface and an opposing second engaging surface (equivalent to first engaging surface 43a and opposing second engaging surface 43b of fitting 32 in (FIG. 12).

Extending radially outwardly from an outer facing surface 39 or the outer perimeter of fitting 32 is access neck portion 70 which provides a portion of bore 34 extending longitudinally therethrough. As shown in FIG. 12, cavity 23 can be accessed through port 34. Although not illustrated, neck portion 70 may be provided by an unitary tube member which is integrally molded into annular ring fitting 32 during molding fabrication. Incidently, similar to the previous configuration, fitting 32 is preferably rigid and may be composed of a number of materials such as polyurethanes, epoxies, silicones, and acrylate polymers like alkaline methacrylates, cyano acrylates, polymethyl methacrylate and poly((2-dimethylamino)ethyl methacrylate. In some instances, it may be preferable to compose fitting 32 from an elastomer, such as polyurethane, so that the seal formed around the edge of the flat sheet device can be slightly deformed to facilitate implantation in certain sites in the body.

Permselective, porous membrane is provided by first sheet membrane 21a and second sheet membrane 21b disposed in opposing relation and spaced apart by fitting 32. As mentioned previously, annular ring fitting 32 may be provided by only a half ring or wedge-shaped ring. In this arrangement, only portions of first sheet membrane 21a are spaced-apart from portions of second sheet membrane 21b (not shown). Both sheet membranes 21a, 21b, cooperate with and seat against respective engaging surfaces of fitting 32 to form a substantially cell-tight dry seal therebetween. Accordingly, first membrane interior surface 22a, second membrane interior surface 22b, and fitting inner surface 48 form storage cavity 23 for holding living cell solution 24 therein. In some circumstances, it may be preferable for the permeability of the first sheet membrane 21a to differ from that of the second sheet membrane 21b. For instance, it may be desirable to control the flow of nutrients through the membranes. The membranes, however, must be impermeable to the living cells.

In accordance with the present invention, the cell-tight dry seal is formed by positioning or sandwiching annular ring 32 between the first and the second sheet membranes in abutting relation so that the respective interior surfaces seat against the respective surfaces of the fitting. During fabrication, as viewed in FIG. 13, a thermoplastic edge portion 71 is preferably molded circumferentially or peripherally around fitting outer facing surface 68 and the perimeter edges 72a, 72b of the first and second sheet membranes, respectively to form an integral unit. This procedure forms a substantial cell-tight "dry" seal all around the peripheral abutting surfaces. Edge portion 71 may comprise a molded polyurethane or other thermoplastic material compatible for bonding with fitting 32 and sheet membranes 21a and 21b. Alternatively, the cell-tight dry seal may be formed by an adhesive which is biocompatible and substantially non-toxic, such as a light-curable acrylate polymer adhesive mentioned above.

Similar to the first configuration, the cell culture solution 24 may be disposed or deposited, through access port 34 in fitting 32, by inserting a syringe needle or the like through port 34 and into the cavity. After deposition of the living cells in cavity 23, any residual solution or contaminants which may have contacted bonding surface 38 of non-porous fitting neck portion 70 may be easily removed therefrom so that the surface becomes "dry".

As best viewed in FIG. 12, plug member 35 is preferably provided by an end cap bonded or attached to bonding surface 38 at a distal end of neck portion 70.

Access port 34, hence, is fully sealed and living cells 24 are encapsulated in storage cavity 23 without affecting their viability. Alternatively, as previously indicated, port 34 may be sealed by applying an acrylic or the like into or over access port 34, or by placing a threaded plug member into port 34 (not shown). Further, fitting 32 may include a hub assembly (not shown), as mentioned above, having a seal member formed to receive a filling tube therethrough.

In another embodiment of the present invention, as shown in FIG. 16, a bead of uncured adhesive may be provided around the outer periphery surface 82 of the hollow fiber membrane 21, proximate second open end 31, to form an adhesive ring 80 which cell-tight "dry" seals with the membrane once cured. After living cells are deposited in the storage cavity, using the above-mentioned techniques, a cell-tight "dry" seal over second open end 31 may be formed, once cured, by applying additional adhesive cap 81 around the end which bonds to adhesive ring 80.

In this arrangement, although adhesive ring 80 need not be fully cured when adhesive cap 81 is bonded thereto, it will be understood that adhesive ring 80 must be sufficiently cured to form cell-tight "dry" seal with the membrane.

In another aspect of the present invention, a method is provided for forming the hollow membrane device configuration which administers a biologically active product or function to an individual. The method comprises the steps of: (a) providing a fitting 32 including an access port 34 extending through the fitting from an outer surface 39 to an inner surface 48; and (b) providing a permselective, porous, membrane 21 having an interior surface 22 cooperating with fitting inner surface 48 to define at least a substantial portion of a storage cavity 23 therebetween. The next step includes: (c) forming a substantially cell-tight, first dry seal between the membrane 21 and an engaging surface 43 of fitting 32; and (d) filling or depositing in cavity 23, through access port 34, living cells 24 capable of secreting a biologically active product or of providing a selected biological function to an individual. The membrane permits the passage of substances between the individual and cells required to provide said biological product or function. The last step includes (d) forming a cell-tight second seal at fitting access, port 34 by providing a plug member 35 formed to cooperate with a bonding surface 38 of fitting 32 to form a cell-tight sealing engagement therewith. As indicated above, the plug member may be provided by fusing the distal end together, sealing the end with a biocompatible adhesive, plugging the open bore with a mating plug or the like.

As best viewed in FIGS. 1A–1C, the filling step may be accomplished by passing a filler tube 54 through access port or open bore 34. Subsequently, lumen 23 may be filled with the living cell solution. Moreover, when a necked hub assembly 44 is provided, the present invention may include the additional steps of passing the filler tube 54 through seal member 50 and through passageway 46 and abutting a distal end 73 of filler tube 54 against an upwardly facing shoulder portion 74 defined by housing 45 and formed to seat filler tube 54 thereagainst. This prevents passage of filler tube 54 into the fitting open bore 34. After depositing the living cells 24 from the filler tube into cavity 23, breaking the frangible neck portion 55 at the frangible region to separate the hub assembly 44 from fitting 32 which causes exposure of the open bore. After separating the hub assembly, providing the plug member 35 over the exposed open bore to cooperate with the bonding surface (distal fitting end 38 and/or fitting inwardly facing surface 33) of the fitting to form the cell-tight sealing engagement therewith.

Another method is provided for forming flat sheet encapsulation device 20 (FIG. 12) to administer a biologically active product or function to an individual. The method comprises the steps of a) positioning a fitting 32 between first interior surface 22a, of first permselective porous membrane 21a, and second interior surface 22b, of a second permselective porous membrane 21b, and (b) forming a first substantially cell-tight dry seal between first membrane 21a and a first engaging surface 43a of fitting 32. The method further includes forming a second substantially cell-tight dry seal between second membrane 21b and a second engaging surface 43b of fitting 32. The fitting inner surface 48, first membrane interior surface 22a and second membrane interior surface 22b cooperate to define storage cavity 23 therein. Living cell solution 24 is then filled or deposited in storage cavity 23, through an access port 34 defined by fitting inwardly facing surface 33 which extends into cavity 23. The method includes forming a third seal at fitting access port 34 by providing a plug member 35 formed to cooperate with a bonding surface 38 of fitting 32 to form a substantially cell-tight sealing engagement therewith.

As provided by the present invention, the step of forming the first substantially cell-tight dry seal (b) and forming second substantially cell-tight dry seal (c) is performed by molding a thermoplastic edge member 71 around outer perimeter edges 72a, 72b, 68 of the first sheet membrane, the second sheet membrane and the fitting, respectively. The molded edge member 71 molding perimeter edges together to form an integral unit and to provide the substantially cell-tight dry seal.

As previously mentioned, a tether portion may be included mounted to the fitting which functions to anchor the encapsulation device to the recipient with the aid of a suture, surgical staple or the like. As shown in FIG. 17, tether portion 65 is mounted to an end of fitting 32 through the support of a tether connector 84 friction fit with the interior surfaces 33, 85 of the respective fitting 32 and tether 65. This arrangement permits the exterior or outer diameter of the tether to be substantially similar to the outer diameter of the fitting. Accordingly, this facilitates insertion of the encapsulation device through a cannula or the like. Further, lodging of the device on tissue during removal thereof can be minimized or reduced. Further, this arrangement may be incorporated on any of the other embodiments set forth above which include plug members.

In this embodiment, after the lumen has been loaded with cell solution (not shown) through open bore 34, one end of connector 84 may be friction fit in fitting bore 34 with an opposite end thereof protruding from the distal end of fitting 32. This connector opposite end is also dimensioned for friction fit into a bore 86 of tubular tether 65 to join the fitting to the tether. Hence, connector 84 not only forms a plug or cell-tight seal of bore 34, but also functions as a joining device with tether 65. Further, while the connector is preferably in frictional engagement with the interior surfaces of the tether bore and the fitting bore, it will be appreciated that the connector may be glued to the fitting and the tether without departing from the true spirit and nature of the present invention.

Preferably, connector 84 is inserted into fitting bore 34 until a recess region 87 thereof is positioned at the juncture between the tether and the fitting. At this juncture, a biocompatible glue or adhesive 88 is preferably applied therebetween to further cell-tight seal bore 34, and fixedly mount or join the tether to the fitting. Recess region 87 is preferably annular shaped and forms a receptical for adhesive 88 to flow therein to contact the interior surfaces 33 and 85 of fitting bore 34 and tether bore 86.

Connector 84 preferably includes a series of rings 89 at the opposite end thereof which enhance friction fit mounting to the interior surface 85 forming tether bore 86. It will be appreciated that in the outer diameter of both ends of connector 84 are dimensioned slightly larger than the internal diameters of fitting bore 34 and tether bore 86 to enable friction fitting therebetween. The connector is relatively rigid to provide support between the fitting and the tether. Further, to enhance imaging of the device, connector 84 is preferably composed of a radio-opaque material such as titanium.

FIGS. 18A and 18B illustrate yet another embodiment of the encapsulation device 20 of the present invention, where tubular fitting 32 is generally flexible and is disposed on one open end 30 of membrane 21. Similar to other embodiments, flexible fitting 32 includes an inwardly facing surface 33 forming open bore 34, and an engaging surface 43 in a cell-tight "dry" sealing engagement with membrane 21 proximate the one open end 30. A bonding surface 75 and an abuttable surface 76 of the fitting cooperate therebetween, upon the application of a solvent to the bonding surface and, optionally, the abuttable surface followed by the application of a washing fluid to the surfaces, to form a cell-tight "wet" sealing engagement upon contact of surfaces together to seal fitting open bore 34.

In the preferred form of this embodiment, fitting 32 is provided by a low durometer hardness polyurethane tubing such as TECOFLEX® by THERMEDICS®. Other suitable biocompatible polymers may include poly(methyl methyacrylate), polycarbonate, polypropylene, silicone or blends thereof.

As viewed in FIGS. 18A and 18B, engaging surface 43 of tubular fitting 32 faces outwardly and forms the substantial cell-tight "dry" seal with membrane interior surface 22. An adhesive layer, such as the two-part polyurethane adhesive (e.g., CasChem 2-part Vorite/Polycin Adhesive) or other biocompatible adhesive, is disposed between fitting engaging surface 43 and membrane interior surface 22 to promote the "dry" sealing. It will of course be appreciated that fitting 32, similar to the other embodiments, could be dry seal mounted to the exterior surface or the distal end of membrane 21 without departing from the true spirit and nature of the present invention.

The encapsulation device 20 includes a hollow fiber having at least on open end and at least one flexible fitting 32 or 32' to be cell-tight sealed. One of the two fittings may be either "wet" sealed or "dry" sealed prior to the deposition of the living cell solution 24. FIG. 18B illustrates that inwardly facing surface 33 of fitting 32 includes both the bonding surface 75 and the abuttable surface 76 in opposed relation therebetween. Hence, after the solvent and washing fluid have been applied to the respective surfaces, contact therebetween is accomplished by compressing the exterior surface of fitting 32 together.

Initially, the solvent will typically induce swelling in the polymer surface. Preferably, the solvent may be chosen as a sterilization liquid, such as a 70% ethanol solution, which partially dissolves the engaging and abuttable surfaces (i.e., interior surface 22) for melding. Exposure to the ethanol solution separates the polymer chains to permit melding of the opposing surfaces during curing. Other solvents, such as isopolypropanol, may be used depending upon which polymer is chosen to compose the fitting.

It will be understood that the solvent does not affect, or is a non-solvent to, the fiber membrane material. Hence, while the inwardly facing surfaces 33 (i.e., the bonding and abuttable surfaces) of the fitting are dissolved, the interior surface 22 providing cavity 23 remain substantially uninfluenced by the solvent.

Preferably, the solvent is ultrafiltered through the pores of membrane 21 as the solvent passes through membrane cavity 23 to "wet" the inwardly facing surfaces. This is used to remove humectant from the pores and to sterilize the device before deposition of the living cell solution 24 therein.

Subsequent to the exposure of the surfaces to the solvent, the exposed surfaces are flushed with a washing fluid. This fluid is chosen as a non-solvent to the fitting which precipitates the dissolved exposed surfaces into a low density three-dimensional structure. In the case of TECOFLEX®, this causes the transparent tubing to turn milky-white in appearance. Such appearance results from the tubing precipitating out of solution into aggregates which diffract the visible light. Preferably, the washing fluid is water or a physiological buffer solution, such as Hanks Buffered Saline Solution.

The prepared fitting ends are then compressed or pinched together, by tweezers, pliers or the like, causing bonding surface 75 to contact abuttable surface 76. In turn, the contact of these low density surfaces allows significant chain interpenetration or "welding" into a permanent seamless homogeneous bulk material under aqueous conditions and without the application of heat.

It will be understood that a cell-tight seal may be formed by folding over or creasing flexible fitting 32 so that two exterior surfaces of the fitting (i.e., an exterior bonding surface and an exterior abuttable surface) come into contact for "welding".

A method is further provided for forming this sealed, implantable, hollow membrane encapsulation device 20 which includes: (a) providing a permselective hollow, porous, membrane 21 including an interior surface 22 defining a storage cavity 23 and one open end 30 providing access into the cavity 23; and (b) forming a cell-tight, first dry seal at open end 30 of membrane 21 between the membrane and an engaging surface 43 of a flexible fitting 32. The method further provides: (c) filling or depositing in cavity 23, through open bore 34, living cells capable of secreting a biologically active product or of providing a selected biological function to an individual; and (d) forming a cell-tight second seal at fitting open bore 34. This second seal is formed by: 1) exposing both the bonding surface 75 and the abuttable surface 76 to a solvent; 2) after the exposing step, washing bonding surface 75 and abuttable surface 76 with a washing fluid; and 3) after the washing step, contacting the bonding surface 75 and the abuttable surface 76 together to form the cell-tight second seal to seal open bore 34.

Preferably, the exposing step and the washing step are accomplished by passing the solvent fluid and subsequently the washing fluid through the open bore of the first fitting 32, and through cavity 23 where it exits through the open pores. This procedure advantageously ultrafilters the fiber membrane.

Further, the exposing step and the washing step are preferably performed before the filling or depositing step so that after deposition of the living cell solution 24 into the cavity, the fitting can be pinched together for "wet" cell-tight sealing.

What is claimed is:

1. A sealed, implantable, encapsulation device for providing a biologically active product or function to an individual, said encapsulation device comprising:

a permselective hollow, porous, membrane shaped so as to form a cell-impervious encapsulating enclosure including an exterior surface, an interior surface and at least one opening, said interior surface defining a storage cavity and said at least one opening providing open communication between said storage cavity and the exterior of said enclosure;

living cells disposed in said cavity capable of secreting a biologically active product or of providing a selected biological function to an individual, said membrane permitting passage therethrough of substances secreted by said cells and required to provide said biological product or function;

a flexible fitting of non-permeable, non-porous material disposed within or about said at least one opening so as to make cell-tight dry sealing engagement with said membrane proximate said at least one opening, said fitting further including an inwardly facing surface defining an access bore extending into said storage cavity, dimensioned so as to permit introduction of living cells into said storage cavity, said fitting further including a bonding surface and an abuttable surface in opposed relation adjacent said open bore, the contact of said surfaces together following application of a solvent for said non-permeable, non-porous material to at least one of said surfaces forming a cell-tight dry seal and closing said at least one opening to the passage of said living cells.

2. The encapsulation device as deformed in claim 1, wherein said membrane comprises a hollow fiber membrane, and said fitting is tubular.

3. The encapsulation device as defined in claim 2, wherein said tubular fitting is disposed within said at least one opening, such that an outer surface or said tubular fitting forms said substantial cell-tight engagement with an interior surface of said membrane to form a cell-tight dry seal of said at least one opening of said hollow fiber membrane enclosure.

4. The encapsulation device as defined in claim 3, further comprising an intermediate adhesive layer between said fitting outer surface and said membrane interior surface.

5. The encapsulation device as defined in claim 4, wherein said inwardly facing surface of said fitting includes said bonding surface and said abuttable surface in opposed relation.

6. The encapsulation device as defined in claim 5, wherein said fitting is composed of polyurethane.

7. The encapsulation device as defined in claim 1, wherein said solvent is a swelling solvent and sterilization liquid for said bonding and abuttable surfaces of said fitting, and a non-solvent for said membrane.

8. The encapsulation device as defined in claim 7, wherein said fitting is composed of polyurethane, and said solvent is ethanol.

9. The encapsulation device as defined in claim 1, wherein said membrane includes two openings, and both said openings have a fitting disposed within each of said openings.

10. A method for forming a sealed, implantable, hollow membrane encapsulation device for providing a biologically active product or function to an individual, said method comprising the steps of:

(a) providing a permselective hollow, porous, membrane shaped so as to form a cell-impervious encapsulating enclosure including an exterior surface, an interior surface and at least one opening, said interior surface defining a storage cavity and said at least one opening providing open communication between said storage cavity and the exterior of said enclosure;

(b) disposing within or about said at least one opening a flexible fitting made of non-permeable, non-porous material and forming a cell-tight, first dry seal between said at least one opening of said membrane said flexible fitting, the fitting including an inwardly facing surface defining an open bore providing communication between the exterior of said enclosure and said cavity and further including, adjacent said open bore, a bonding surface and an abuttable surface in opposed relation;

(c) depositing in said cavity, through said open bore, living cells capable of secreting a biologically active product or of providing a selected biological function to an individual, said membrane permitting passage therethrough of substances secreted by said cells and required to provide said biological product or function; and (d) exposing at least one of said bonding surface and said abuttable surface of said flexible fitting to a solvent for said material, then contacting said bonding surface and said abuttable surface together to form a cell-tight second seal which closes said open bore.

11. The method of claim 10, wherein, after said exposing step, each surface thus exposed to a solvent is further exposed to a washing fluid before contacting said bonding and abuttable surfaces together.

12. The method of claim 11, wherein said bonding surface and said abuttable surface in opposed relation are contacted by compressing said fitting until said bonding surface and said abuttable surface come together.

13. The method of claim 12, wherein said exposing steps are performed before said depositing step (c).

14. The method of claim 11, wherein said solvent is a swelling solvent and sterilization liquid for said fitting but a non-solvent for said membrane, and said washing fluid is a precipitating solvent and a humectant removal liquid.

15. The method of claim 14, wherein said fitting is composed of polyurethane, said solvent is ethanol, and said washing fluid is water.

16. The method of claim 11, wherein said exposing steps are accomplished by passing said solvent and said washing fluid through said open bore.

17. The method of claim 16, wherein said solvent is a non-solvent to said membrane, and said solvent is ultrafiltered through the membrane.

* * * * *